United States Patent
Bhandari et al.

[11] Patent Number: 6,102,993
[45] Date of Patent: Aug. 15, 2000

[54] COPPER PRECURSOR COMPOSITION AND PROCESS FOR MANUFACTURE OF MICROELECTRONIC DEVICE STRUCTURES

[75] Inventors: Gautam Bhandari, Danbury; Thomas H. Baum, New Fairfield; Chongying Xu, New Milford, all of Conn.

[73] Assignee: Advanced Technology Materials, Inc., Danbury, Conn.

[21] Appl. No.: 09/365,913

[22] Filed: Aug. 3, 1999

Related U.S. Application Data

[60] Provisional application No. 60/095,057, Aug. 3, 1998.

[51] Int. Cl.$^7$ ............ C23C 16/18; C09K 3/00; C07F 1/08; C07F 7/08; B05D 5/12

[52] U.S. Cl. ............ 106/1.18; 106/287.14; 106/287.18; 106/286.7; 438/687; 427/124; 427/248.1; 427/250; 556/12; 556/110; 556/112; 556/117; 556/465

[58] Field of Search ............ 106/1.05, 1.18, 106/286.7, 287.14, 287.18; 438/687; 427/124, 248.1, 250; 556/12, 110, 112, 117, 465

[56] References Cited

U.S. PATENT DOCUMENTS

| | | | |
|---|---|---|---|
| Re. 35,614 | 9/1997 | Norman | 427/250 |
| 3,356,527 | 12/1967 | Moshier et al. | |
| 3,594,216 | 7/1971 | Charles et al. | 117/107.2 |
| 4,908,065 | 3/1990 | Tanitsu et al. | 106/287.18 |
| 5,085,731 | 2/1992 | Norman et al. | 427/250 |
| 5,094,701 | 3/1992 | Norman | 148/23 |
| 5,097,737 | 3/1992 | Uhrig | 84/314 N |
| 5,098,516 | 3/1992 | Norman et al. | 427/250 |
| 5,144,049 | 9/1992 | Norman et al. | 556/12 |
| 5,187,300 | 2/1993 | Norman | 556/12 |
| 5,220,044 | 6/1993 | Baum | 556/40 |
| 5,322,712 | 6/1994 | Norman et al. | 427/250 |
| 5,449,799 | 9/1995 | Terfloth et al. | 556/112 |
| 5,527,739 | 6/1996 | Parrillo et al. | 438/687 |
| 5,744,192 | 4/1998 | Nguyen et al. | 427/250 |
| 5,767,301 | 6/1998 | Senazaki et al. | 556/117 |
| 5,820,664 | 10/1998 | Gardiner et al. | 106/287.17 |

FOREIGN PATENT DOCUMENTS

WO 98/40387 of 0000 France.

OTHER PUBLICATIONS

R.L. Van Hemert et al., "Vapor Deposition of Metals by Hydrogen Reduction of Metal Chelates" J. Electrochemical Soc. (112), 1123 (1965); no month available.

Reisman et al., "Chemical Vapor Deposition of Copper from Copper(II) Hexafluoroacetonate", J. Electrochemical Soc., vol. 136, No. 11, (Nov. 1989).

A.E. Kaloyeros et al., "Low Temperature Metal–Organic Chemical Vapor Deposition (LTMOCVD) of Device–Quality Copper Films for Microelectronic Applications" J. Electronic Materials, vol. 19, No. 3, p. 271 (1990); no month available.

Oehr H. Suhr, "Thin Copper Films by Plasma CVD Using Copper–Hexafluoro–Acetylacetonate", Applied Phys. A. (45) 151–154 (1988); no month available.

Houle et al., "Laser Chemical Vapor Deposition of Copper", Appl Phys. Lett. (46) pp. 204–206 (1985); no month available.

(List continued on next page.)

*Primary Examiner*—Helene Klemanski
*Attorney, Agent, or Firm*—Oliver A. M. Zitzmann; Steven J. Hultquist

[57] ABSTRACT

Copper precursor formulations, including a copper precursor with at least one of (a) water, (b) a water precursor and (c) a non-ligand organic hydrate, are useful in CVD processes, e.g., in liquid delivery chemical vapor deposition, for forming a copper-containing material on a substrate. The disclosed copper precursor formulations are particularly useful in the formation of copper layers in semiconductor integrated circuits, e.g., for metallization of interconnections in such semiconductor device structures.

59 Claims, 2 Drawing Sheets

OTHER PUBLICATIONS

Awaya et al., "Deposition Mechanism of Copper CVD" Conf. Proc., VLSI–VII (1992); MRS, p. 345; no month available.

Patrick M. Jeffries et al., "Chemical Vapor Deposition of Copper and Copper Oxide Thin Films from Copper (I) tert–Butoxide" Chem. Mater. (1) pp. 8–10 (1989), no month available.

Norman et al., "New OMCVD Precursors for Selective Copper Metallization" Journal De Physique IV, Colloque C2, suppl. Au Journal de Physique II, vol. 1, 271–278, (Sept. 1991).

Beach et al., "Low Temperature Chemical Vapor Deposition of High Purity Copper from an Organometallic Source", Chem. Mater., 1990, 2, 216–219, no month available.

Shin et al., Selective Low–Temperature Chemical Vapor Deposition of Copper form (Hexafluoroacetylacetanato-)copper(I)trimethylphosphine, (hfa)CuP(Me)$_3$, Adv. Mate. 3 (1991) No. 5, pp. 246–248, no month available.

Hampden–Smith et al., "Chemical Vapor Deposition of Copper from Copper(I) Trimethylphosphine Compounds", Chem. Mater., 1990 (2) 636–639, no month available.

COPPER PRECURSOR COMPOSITION AND PROCESS FOR MANUFACTURE OF MICROELECTRONIC DEVICE STRUCTURES

CROSS-REFERENCE TO RELATED APPLICATION

This claims the priority of U.S. Provisional patent Application No. 60/095,057, filed Aug. 3, 1998 in the names of Gautman Bhandari, Thomas H. Baum and Chongying Xu for "COMPOSITION AND PROCESS FOR PRODUCTION OF COPPER LAYERS IN INTEGRATED CIRCUITS."

BACKGROUND OF THE INVENTION

1. Field of the Invention

The present invention relates to copper precursor compositions and their synthesis, and to a method for fabricating copper-containing microelectronic device structures such as in formation of metal interconnects for the manufacture of semiconductor integrated circuits, or otherwise for metallizing or forming copper-containing films on a substrate by metalorganic chemical vapor deposition (MOCVD) utilizing such precursor compositions.

2. Description of the Related Art

The process of fabricating semiconductor integrated circuits generally includes the formation of metal interconnect lines. The metal interconnect lines often may be formed from multiple conductive layers. For example, a thin conductive layer generally termed a barrier layer may be formed from a metal or metal suicide and a thicker conductive layer formed from a conductive material, for example aluminum, may be formed on the barrier layer.

In order to enhance circuit speed performance and reduce electro-migration effects, the use of copper layers has been proposed to replace the use of aluminum layers. Thus one or more metal layers of a semiconductor integrated circuit may be formed utilizing a copper-based layer. Copper is of great interest for use in metallization of VLSI devices because of its low resistivity, low contact resistance, and ability to enhance device performance through the reduction of RC time delays. Many semiconductor device manufacturers are adopting copper metallization for use in production of microelectronic chips.

Chemical vapor deposition (CVD) is a potentially useful technique for metallization in the fabrication of microelectronic device structures, e.g., liquid delivery metalorganic chemical vapor deposition (MOCVD), wherein liquid precursor material is introduced to a vaporizer unit including a heated vaporization element and volatilized at high rate ("flash vaporized") in contact with the heated vaporization element to form a precursor vapor. The precursor vapor then is contacted with a substrate at sufficient elevated temperature to deposit a metal-containing film on the substrate from the precursor vapor.

Liquid delivery MOCVD is a highly useful technique for formation of metal-containing films on substrates. In application to metallization in microelectronic device structures, the accuracy and precision of the delivery rate of precursor in liquid delivery MOCVD that is achievable using volumetric metering and other monitoring and process control aspects of liquid delivery MOCVD technology, in turn enables commercial reproducibility to be attained in the metallization operation for very large scale integration (VLSI) device manufacture.

Liquid delivery MOCVD, however, requires liquid precursor compositions. Such compositions may comprise source reagent compounds or complexes that are themselves liquids, or alternatively the precursor composition may comprise compounds or complexes that are dissolved or suspended in a suitable liquid solvent medium. Advantageous liquid precursor compositions are desirably stable at ambient temperature (e.g., in the range of 10–40° C.) conditions, for extended periods of time, to accommodate transportation and storage of such compositions subsequent to their manufacture and prior to their use.

Although the use of copper precursors in MOCVD to create copper interconnects in semiconductor integrated circuits is known (see, e.g., U.S. Pat. Nos. 5,085,731; 5,098,516; 5,144,049; and 5,322,712; and the references cited therein), only a few liquid copper precursors are commercially available. These include (hfac)Cu(MHY), (hfac)Cu(3-hexyne), (hfac)Cu(DMCOD) and (hfac)Cu(VTMS), wherein hfac=1,1,1,5,5,5-hexafluoroacetylacetonato, MHY=2-methyl-1-hexen-3-yne, DMCOD=dimethylcyclooctadiene, and TMVS=trimethylvinylsilane.

New and useful compositions and processes for the production of copper that improve on, or provide alternatives to, these known compositions would be highly desirable for large-scale manufacture of integrated circuits, including formation of copper on the microelectronic device substrate (i) as a conductive thin-film plating base layer for subsequent electroplating of metal thereon, and/or (ii) in so-called "full-fill" deposition of copper for forming interconnects and other elements of microelectronic device structures.

In the first such application, of forming a copper film plating base, or seed layer, for subsequent electroplating, the copper film must have low resistivity and uniform thickness, to achieve uniform current density in the electroplating operation. The copper film also must be of a uniform conformability character to accommodate the high aspect ratio features, complex geometries and damascene processing involved in VLSI device manufacture. Finally, the copper film must have excellent adhesion to the barrier layer.

The copper precursor currently most widely used in semiconductor device manufacture is the aforementioned (hfac)Cu(TMVS), commercially available as CupraSelect (Schumacher Division of Air Products & Chemicals, Inc., Allentown, Pa.). This precursor, however, suffers from inherently poor thermal stability and therefore requires additives to enhance the molecule's physical properties, including thermal stability, and to facilitate uniform nucleation and film growth.

By way of example, Norman et al. U.S. Pat. No. 5,322,712 teaches that improved quality copper films are produced in the MOCVD usage of (hfac)Cu(TMVS) when a volatile ligand or ligand hydrate, e.g., hexafluoro-2,4-pentanedionate hydrate is introduced into the CVD reactor with vapors of the (hfac)Cu(TMVS) precursor. The Norman et al. patent does not describe the use of a liquid delivery flash vaporization technique in connection with the precursor compositions therein disclosed. Instead, the patent teaches to employ a low pressure evaporation chamber to evaporate the ligand or ligand hydrate under reduced pressure, with the (hfac)Cu(TMVS) being volatilized in a bubbler or the same type low pressure evaporation chamber as the ligand or ligand hydrate.

The additives disclosed in the Norman et al. patent, however, may lead to contamination of the copper film, either during nucleation or steady-state film growth. In both cases, the electrical properties of the film may be compromised, resulting in high film resistivity and/or high contact resistance. In multi-layered structures, such electrical properties are critical to device integration and manufacture.

Such contamination of the product film incident to the use of the ligand or ligand hydrate as additives in accordance with the Norman et al. patent is attributable to the fact that the ligand is susceptible to decomposition during the film growth process, especially at the barrier-copper interface. In addition, over time precursors such as (hfac)Cu(TMVS) show decomposition to green Cu(II) species. These are significant deficiencies of the prior art.

The prior art (in N. Awaya, et al., Conf. Proc. ULSI-VII 1992 MRS, p.345) has disclosed that water vapor can accelerate the deposition of copper from CVD precursors, and the aforementioned Norman et al. patent discloses the addition of 50 ppm of water vapor to pure, dry (hfac)Cu (TMVS) under oxygen-free CVD conditions to show the resultant formation of Hhfac. Such steam injection operation of the MOCVD system, however, requires a separate boiler and feed water source as well as associated injection means, and increases the cost and complexity of the MOCVD process system.

There is therefore a need in the art for new and improved copper precursor compositions and methods for use in the manufacture of integrated circuits and other microelectronic device structures, using techniques such as chemical vapor deposition, plasma-assisted CVD, etc., and particularly liquid delivery MOCVD.

It is accordingly an object of the present invention to provide new copper precursors.

It is another object of the invention to provide a method of depositing copper in the manufacture of integrated circuits and other microelectronic device structures, utilizing such copper precursors.

It is a further object of the invention to provide metallization precursor compositions and methodology for forming interconnects and other device structures, which overcome the shortcomings and limitations of the prior art.

Other objects and advantages of the present invention will be more fully apparent from the ensuing disclosure and appended claims.

SUMMARY OF THE INVENTION

The present invention relates in one compositional aspect thereof to a composition comprising:
(i) a copper precursor; and
(ii) at least one of (a) water, (b) a water precursor and (c) a non-ligand organic hydrate.

Such aspect of the invention provides unexpected improvements, e.g., increase in deposition rate, improvement in quality of copper, reduction in copper impurities, reduction in problems associated with copper precursor decomposition that may detrimentally occur at or near the barrier-copper interface; decomposition of Cu(I) precursors to Cu(II) compounds, and so forth.

In another respect, the invention relates to a process for the deposition of copper on a substrate, comprising carrying out chemical vapor deposition using a composition of the type described hereinabove. This aspect of the invention also relates to the copper made by the process of the present invention as well as integrated circuits made using such process.

In yet another aspect, this invention relates to a process of making a composition for CVD of copper, including combining a copper precursor with at least one of (a) water, (b) a water precursor and (c) a non-ligand organic hydrate.

As used herein, the term "non-ligand" in reference to the organic hydrate means that the organic hydrate does not comprise a hydrated form of a ligand of the copper precursor. The copper precursor is typically in the form of a copper-containing compound or complex in which copper atom(s) is/are covalently bound to or otherwise coordinatively associated with one or more ligand moieties. The ligand moieties are typically organo moieties. Accordingly, organic hydrates used as an adjuvants in compositions according to the present invention are not corresponding hydrates of such organo ligand moieties of the copper precursor, but are independent and distinct hydrate components in such compositions.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
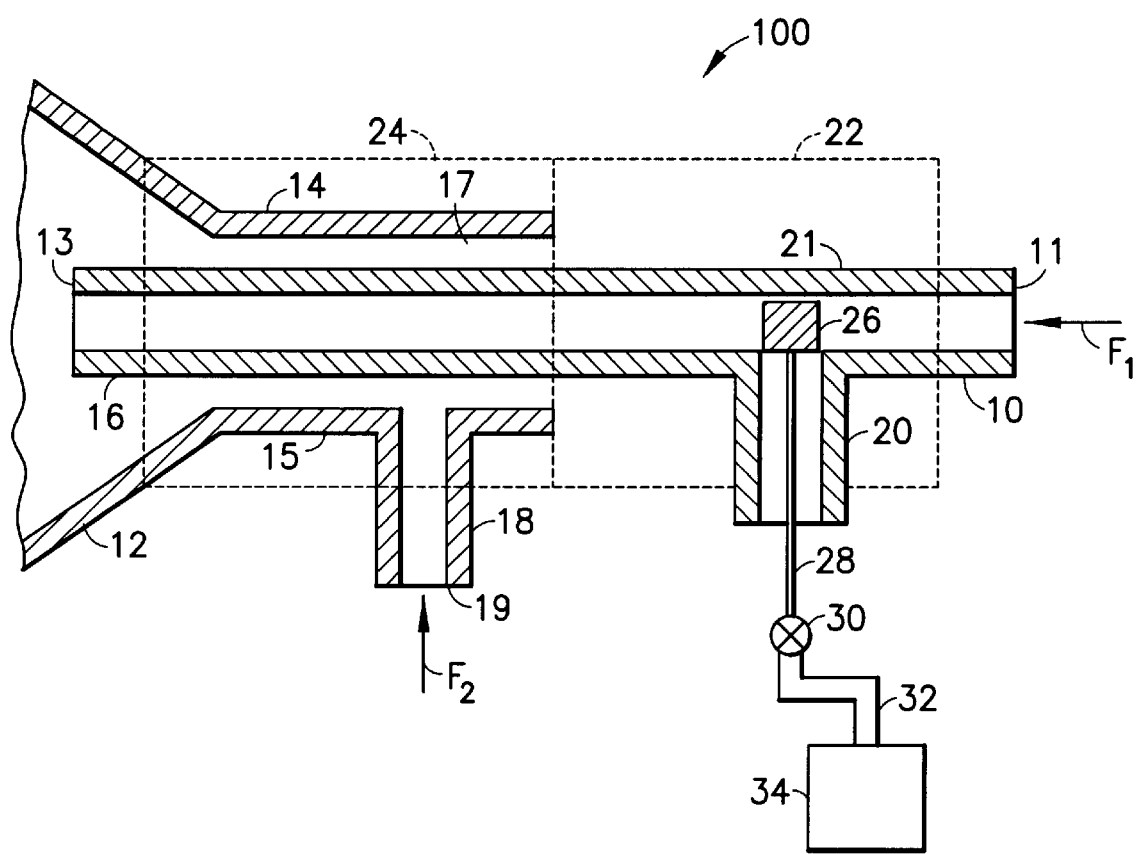
FIG. 1 is a schematic representation of a liquid delivery and vaporization system as may be used with a chemical vapor deposition (CVD) chamber for the deposition of copper-containing material on a substrate in accordance with the present invention.

The copper precursors that may be used in the practice of this invention include, but are not limited to, the copper compounds and complexes described in U.S. Pat. Nos. 5,085,731; 5,094,701; 5,098,516; 5,144,049; 5,322,712; 3,356,527; and 3,594,216 and in R. L. Van Hemert et al., J. Electrochemical Soc. (112), 1123 (1965); Reisman et al., J. Electrochemical Soc., Vol. 136, No. 11, (November 1989); A. E. Kaloyeros et al., J. Electronic Materials, Vol. 19, No. 3, p. 271 (1990); Oehr H. Suhr, Applied Phys. A. (45) 151–154 (1988); Houle et al., Appl Phys. Lett. (46) pp. 204–206 (1985); Awaya et al., Conf. Proc., VLSI-VII (1992); MRS, p. 345; Girolami et al., Chem. Mater. (1) pp. 8–10 (1989); and Norman et al., E-MRS Proc. B17, pp. 87–92 (1993), the entire contents of which are incorporated by reference. Non-limiting, representative copper precursors include Cu(II)bis(acetylacetonate) Cu(II)(acac)$_2$, Cu(II)bis (hexafluoracetylacetonate) (i.e., (Cu(II)(hfac)$_2$), Cu(I) hfac.2-methyl-1-hexen-3-yne ("Cu(I)hfac.MHY" or "(hfac)Cu(MHY)"), Cu(I)hfac.trimethylvinylsilane (i.e., (hfac)Cu TMVS) and copper complexes of formula I:

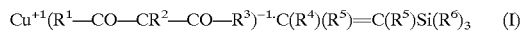

wherein $R^1$ and $R^3$ are each independently $C_1$–$C_8$ perfluoroalkyl, $R^2$ is H, F or $C_1$–$C_8$ perfluoralkyl, $R^4$ is H, $C_1$–$C_8$ alkyl, or $Si(R^6)_3$, each $R^5$ is independently H or $C_1$–$C_8$ alkyl, and each $R^6$ is independently phenyl or $C_1$–$C_8$ alkyl. The complexes of formula I may be made using the procedures set forth in U.S. Pat. No. 5,144,049 and references cited therein.

Apart from the foregoing, the disclosures of the following United States patents and patent applications are hereby incorporated herein by reference in their entireties:
U.S. patent application Ser. No. 08/835,768 filed Apr. 8, 1997 in the names of Thomas H. Baum, et al., now issued as U.S. Pat. No. 5,919,522;

U.S. patent application Ser. No. 08/414,504 filed Mar. 31, 1995 in the names of Robin A. Gardiner et al., now issued as U.S. Pat. No. 5,820,664;

U.S. application Ser. No. 08/280,143 filed Jul. 25, 1994, in the names of Peter S. Kirlin, et al., now issued as U.S. Pat. No. 5,556,323;

U.S. patent application Ser. No. 07/927,134, filed Aug. 7, 1992 in the same names, now abandoned;

U.S. patent application Ser. No. 07/807,807, filed Dec. 13, 1991 in the names of Peter S. Kirlin, et al., now issued as U.S. Pat. No. 5,204,314;

U.S. application Ser. No. 08/181,800 filed Jan. 15, 1994 in the names of Peter S. Kirlin, et al., and issued as U.S. Pat. No. 5,453,494;

U.S. application Ser. No. 07/918,141 filed Jul. 22, 1992 in the names of Peter S. Kirlin, et al., and issued Jan. 18, 1994 as U.S. Pat. No. 5,280,012;

U.S. application Ser. No. 07/615,303 filed Nov. 19, 1990, now abandoned;

U.S. application Ser. No. 07/581,631 filed Sep. 12, 1990 in the names of Peter S. Kirlin, et al., and issued Jul. 6, 1993 as U.S. Pat. No. 5,225,561; and U.S. patent application Ser. No. 07/549,389 filed Jul. 6, 1990 in the names of Peter S. Kirlin, et al., now abandoned.

The present invention is based on the discovery that copper precursors useful for the CVD formation of copper-containing films on substrates, such as liquid delivery MOCVD formation of copper metallization and copper-containing elements in microelectronic device structures, can be substantially improved by incorporating a non-ligand hydrating component in the precursor formulation. The benefits attendant the incorporation of such non-ligand hydrating component, as mentioned hereinabove in the "Summary of the Invention" section hereof, are dependent on the specific embodiment of the invention, but variously include beneficial improvements in deposition rate of the copper-containing film, quality of the copper that is deposited, reduction of impurities in the deposited copper, character of the interface of the copper-containing film and an associated barrier layer, incidence of decomposition of copper (I) precursors to copper (II) compounds, etc.

In contrast to the hydrated ligand approach of Norman et al. U.S. Pat. No. 5,322,712, which in the case of fluorine-containing ligands such as hfac can adversely increase the extent of fluorine incorporation in the product film, the present invention permits the use of non-ligand organic hydrates which are free of such deficiencies. The Norman et al. patent teachings of using a hydrated ligand as an adjuvant have been viewed as providing a compatible ligand chemistry that is necessary for achieving the film improvements disclosed by Norman et al., as an alternative to the injection of steam into the CVD reactor, particularly since the view of the CVD art has been that water or moisture in the CVD precursor is to be avoided.

Such avoidance of water or moisture in the CVD precursor has been the conventional wisdom approach in the art, in order to avoid side or competing reactions that would reduce the efficiency of the CVD process, as well as a general bias that water in any form was deleterious in the precursor composition, which typically is organic in constitution. Such approach and bias (of avoidance of water and moisture) has been particularly entrenched in the liquid delivery MOCVD field, where the occurrence of side and competing reactions and presence of impurities has been found to substantially increase the nature and extent of unwanted solids deposition in the flash vaporization chamber of the liquid delivery MOCVD process system.

Against these fears of potential detriment, it has surprisingly and unexpectedly been found that "hydration" of the deposition step in the CVD reactor can be effected, with the associated benefits disclosed in the Norman et al. patent and discussed hereinabove, by the variant approaches of the present invention, according to which a "hydrative" formulation of the copper precursor is employed in the CVD process, without steam injection to the CVD reactor and without the requirement of using a hydrated ligand as taught in the Norman et al. patent.

Further, by avoiding the hydrated fluorinated ligands of the Norman et al. patent, and using non-fluorinated water precursors in accordance with a preferred aspect of the present invention, it has been found to be possible to significantly reduce fluorine content in the copper films formed from precursor formulations of the present invention, by up to 2% by weight, in relation to fluorine content of films correspondingly formed without the presence of such water precursor.

Such hydrative copper precursor formulations of the present invention comprise:

(iii) a copper precursor; and
(iv) at least one of (a) water, (b) a water precursor and (c) a non-ligand organic hydrate.

The CVD usage of the copper precursor formulations of the present invention provides unexpected improvements, e.g., increase in deposition rate of the copper-containing film deposited on the substrate, improvement in the quality of the deposited copper-containing film, reduction in the concentration and/or variety of film impurities, reduction in the problems associated with copper precursor decomposition that may detrimentally occur at or near the barrier-copper interface; reduction or elimination of the decomposition of Cu(I) precursors to Cu(II) compounds during use of the precursor composition in the CVD process, and so forth.

The copper precursor formulations of the present invention are readily made up by combining the specific copper precursor(s) with at least one of (a) water, (b) a water precursor and (c) a non-ligand organic hydrate, using conventional blending or mixing means, to yield the product formulation. Such blending or mixing means may illustratively include, without limitation, mechanical mixers, blenders, sonication mixing means, shakers, spargers, impulse-mixing and momentum-based mixing means, etc.

In one embodiment of this invention, the copper precursor composition may be hydrated by incorporating in the composition a sterically crowded (sterically hindered) organic moiety that is capable of decomposing to yield water and a volatile organic by-product under use conditions in the CVD process. The decomposition of the water precursor component in the copper precursor formulation may occur during the chemical vapor deposition step of the process, thereby facilitating the benefits of the presence of water during CVD and being substantially free of undue side effects. The water-releasing decomposition (dehydration) reaction may for example be carried out in accordance with the following reaction scheme: $2\ R^7OH \rightarrow R^7OR^7 + H_2O$, wherein $R^7$ may be, for example, $C_1$–$C_5$ alkyl, or alkylsilyl groups such as $(Me)_3Si$, $(Me)_x(R_A)_{(3-x)}Si$, where $R_A$ is $C_1$–$C_5$ alkyl, and the like.

Generally, the decomposition of the hydration precursor may take place by an inter- or an intra-molecular reaction. The sterically hindered organic moiety (the water precursor) may be mixed together with the copper precursor prior to being introduced into a CVD reactor, or alternatively may be introduced to the CVD reactor separately from the copper precursor. The water precursor is preferably formulated with the copper precursor in a composition that may optionally further comprise stabilizers, solvating, solubilizing or suspending agents, surfactants, uv absorbers, etc.

As mentioned hereinabove, the water precursor in accordance with the present invention is preferably non-fluorinated in character, and thereby achieves a substantial improvement in the quality of the product copper film, as regards the fluorine content thereof, in relation to product copper films produced using the hydrated hfac ligand taught by the Norman et al. patent.

The amount of water precursor employed in the copper precursor formulation may be widely varied in the broad practice of the invention, depending on type of moiety and desired amount of water to be delivered. In general, the amount of water precursor used is any amount that will decompose to produce water, preferably an amount of water that produces one or more of the aforementioned beneficial effects such as an improved rate of copper deposition from the precursor vapor.

In another embodiment of the present invention, a non-ligand organic hydrate is used as the hydrating component in the copper precursor formulation. Non-limiting, representative examples of such organic hydrates include hydrates formed from cyclic and acyclic organic compounds having ketone groups, hydroxy groups, amino groups, and combinations thereof, especially non-fluorinated compounds. Non-limiting, representative examples of such organic compounds include those of the formulae below:

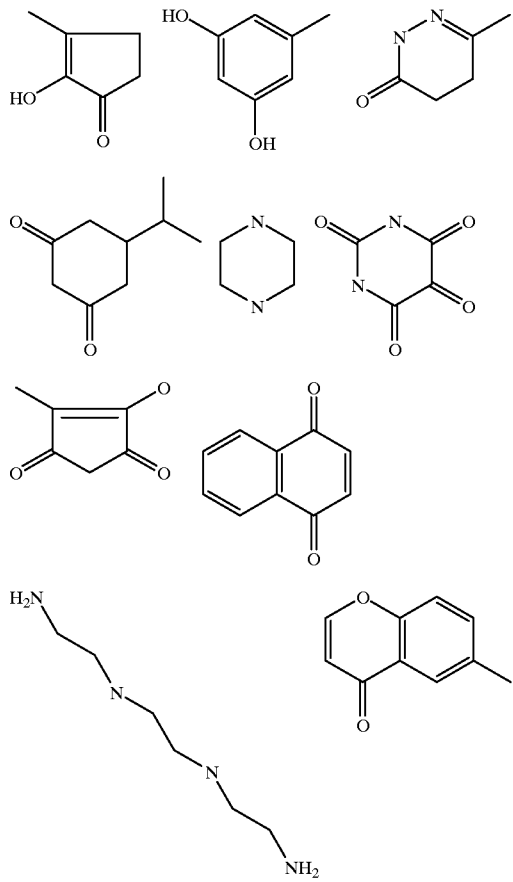

-continued

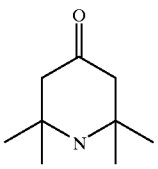

The amount of water employed to form the hydrate may vary widely, but in general is greater than zero and less than ten water molecules per molecule of organic compound, and more typically from about one to about six water molecules per molecule of organic compound. In general, the amount of organic hydrate used in the copper precursor formulation is any amount that will dehydrate to produce water, preferably in an amount of water that produces one or more of the aforementioned beneficial effects such as an improved rate of copper deposition from the precursor vapor. The organic hydrate in an illustrative embodiment of the invention may be present in the copper precursor formulation in an amount of from about 2 to about 15% by volume, based on the volume of the formulation. The formulation containing the organic hydrate may further comprise additional components, e.g., solvating, solubilizing or suspending agents, stabilizers, etc., as in the case of the water precursor-containing formulations discussed above.

In yet another embodiment of this invention, water, a solubilizing agent, and the copper precursor are mixed to form the formulation, preferably as a homogeneous composition. The mixing of the water, solubilizing agent and copper precursor components can occur in any order and by any method, and is typically carried out by mixing the water and solubilizing agent under gentle mechanical agitation, and then adding the water/solubilizing agent mixture to the copper precursor, again under gentle mechanical agitation, such as with a paddle mixer or a magnetic stirrer.

The solubilizing agent may be, for example: an alcohol, e.g., of the formula $R^aOH$ where $R^a$ is $C_1$–$C_8$ alkyl, such as methanol, ethanol, isopropanol, tert-butanol or neopentanol; ether(s) such as those of the formula $R^8$—O—$R^8$ or $R^8$—O—$R^*$—O—$R^8$ where $R^8$ is $C_1$–$C_5$ alkyl and $R^*$ is $C_1$–$C_6$ alkylene; trioxane; or a ketone such as those of the formula $R^8$—CO—$R^8$ where $R^8$ is $C_1$–$C_5$ alkyl. The composition containing water, solubilizing agent, and copper precursor may be of any proportion, as regards the relative amounts of the water, solubilizing agent and copper precursor. Typically, the composition contains an amount of water that produces one or more of the aforementioned beneficial effects such as an improved rate of copper deposition from the precursor vapor, with the amount of solubilizing agent being preferably sufficient to substantially solubilize the water and copper precursor.

Since U.S. Pat. No. 5,144,049 for instance, indicates that the copper complexes are water-sensitive, it is surprising that the compositions according to the invention, containing copper precursor, water, and solubilizing agent have been found to be quite stable.

The copper precursor formulations of the present invention may be widely varied and constituted, as regards the copper precursor components thereof. The copper precursor formulation of the invention may for example contain at least one copper precursor, such as for example Cu(II)(acac)$_2$, (hfac)Cu(MHY), (hfac)Cu(3-hexyne), (hfac)Cu(DMCOD) or (hfac)Cu(TMVS).

In the case where the copper precursor formulation contains (hfac)Cu(TMVS), such copper precursor formulation preferably does not contain:

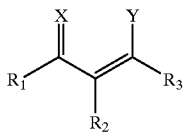

wherein $R_1$ and $R_3$ are independently selected from alkyl, aryl, fluoroalkyl or fluoroaryl; $R_2$ is halogen, alkyl, aryl, fluoroalkyl, or fluoroaryl; X and Y are selected such that when X=O, Y is OH, $NH_2$ or $N(R_4)H$, when X=NH, Y is $NH_2$ or $N(R_4)H$, when X=$NR_5$, Y is $(R_4)H$, and $R_4$ and $R_5$ are selected from the group consisting of alkyl, aryl, fluoroalkyl and fluoroaryl.

In general, the copper precursor formulations of the invention may be formulated to comprise, consist of, or consist essentially of any appropriate components herein disclosed, and such copper precursor compositions of the invention may additionally, or alternatively, be formulated to be devoid, or substantially free, of any components taught to be necessary in prior art formulations that are not necessary to the achievement of the objects of the invention hereunder.

The copper precursor formulations of the present invention may be usefully employed in a variety of applications. For example, a copper precursor formulation of the invention may be utilized to form copper interconnect lines in a semiconductor integrated circuit. To fabricate such integrated circuits, the semiconductor substrate may have a number of dielectric and conductive layers formed on and/or within the substrate.

As used herein, the semiconductor substrate may include a bare substrate or base structure, or the substrate may alternatively comprise such bare substrate or base structure, on which and/or within which have been formed or provided one or more layers, features, differentiated regions, microelectronic elements or precursor structures.

Using a copper precursor formulation according to the present invention, a copper-containing layer may be formed on the semiconductor substrate for use in a first, second, third, or additional metallization layer. Such copper layers may be used in circuit locations requiring low resistive and/or high speed circuit paths, and the copper layer is typically deposited on a barrier layer on the substrate.

Copper-containing films may thus be readily deposited on the substrate, using a copper precursor formulation of the present invention in a CVD process system of any suitable type, e.g., a low pressure MOCVD system. Preferably the CVD process system is a liquid delivery CVD process system, such systems being well known in the semiconductor fabrication art. The copper precursor compositions of the invention may alternatively be utilized in other deposition process systems, e.g., plasma enhanced chemical vapor deposition (PECVD) systems, other enhanced or assisted CVD process systems, dopant systems for implantation of copper, etc.

In CVD applications, the copper precursor formulation may be volatilized and transported to the deposition chamber (CVD reactor) in any suitable manner. Such formulation is advantageously utilized in a liquid delivery system, as for example a liquid delivery system utilizing mass flow controllers (MFCs) or other precision flow control means for precise metering of the copper precursor in liquid form to a vaporizer, where the precursor is volatilized to form the precursor vapor which subsequently is contacted with the substrate at elevated temperature to deposit the desired metal-containing film. An illustrative liquid delivery system of such type is the ADCS Sparta 150 Liquid Delivery System, commercially available from Advanced Technology Materials, Inc. (Danbury, Conn.). Liquid delivery systems are variously described in U.S. Pat. Nos. 5,204,314; 5,362,328; 5,536,323; and 5,711,816, the disclosures of which are expressly incorporated herein by reference in their respective entireties.

Although the precursor formulations disclosed herein have been described as being usefully employed in liquid delivery systems, it will be appreciated that other means and methods may be employed to deliver the formulation to the process tool, e.g., bubbler-based delivery systems. In bubbler systems, an inert carrier gas may be bubbled through a volume of the precursor formulation in a suitable containment vessel and the resulting gas, which is wholly or partially saturated with the vapor of the formulation, is then transported to the CVD tool.

A wide variety of CVD process conditions may be employed for the formation of copper-containing films on substrates, using the compositions of the present invention. Illustrative process conditions may for example include: substrate temperature ranges of from about 160° C. to about 230° C., with substrate temperatures of from about 190° C. to about 200° C. being more typical; vaporizer temperature ranges of about 100° C. to about 300° C., with temperatures of from about 65° C. to about 90° C. being more typical; pressure ranges of from about 0.05 to about 20 Torr, with a range of from about 0.2 to about 0.5 Torr being more typical, and most preferably about 0.5 Torr; and inert gas flows of helium or argon at a flow rate of from about 25 to about 750 sccm, and most preferably 100 sccm, at a temperature that is approximately the same as the temperature of the vaporizer in operation during active processing.

The following examples are representative of specific aspects of the invention and are not intended to limit the scope of the invention or claims hereto. In all instances, (hfac)Cu(I)MHY, wherein MHY is 2-methyl-1-hexen-3-yne, was prepared using standard techniques.

EXAMPLE I

A mixture of (hfac)Cu(MHY) with approximately 2% water was well-shaken, then allowed to stand at room temperature under a nitrogen atmosphere. After a week, no decomposition was observed, but immiscible water droplets were observed.

EXAMPLE II

One drop of methanol/water (1:1) was added to one gram of (hfac)Cu(MHY). The resultant concentration of water/methanol was about 2% of the (hfac)Cu(MHY). The mixture was well shaken, then allowed to stand at room temperature under nitrogen atmosphere. After 3 days, no decomposition was observed, but immiscible droplets were observed. After 2 more drops of methanol were added, the mixture became a clear, homogenous solution.

EXAMPLE III

One drop of acetone/water (1:1) was added to one gram of (hfac)Cu(MHY). The water/acetone concentration in the resultant mixture was about 2% of the (hfac)Cu(MHY). The mixture was well shaken, then allowed to stand at room temperature under nitrogen atmosphere. After 3 days, no decomposition appeared to have taken place, but immiscible droplets were observed. After 2 more drops of acetone were added, the mixture was still immiscible.

EXAMPLE IV

One drop of trioxane/water (1:5) was added to one gram of (hfac)Cu(MHY). An immiscible mixture was obtained.

EXAMPLE V

Two drops of water-saturated dimethoxymethane were added to one gram of (hfac)Cu(MHY). A clear, homogeneous solution was obtained.

The foregoing examples reflect the stability of the copper precursor formulations of the present invention. While Examples I, III and IV relate to formulations that are immiscible in character, it will be appreciated that such formulations may be further modified with surfactants, solubilizing agents, additional solvent components, etc., to provide a desired miscible character to the formulation, within the broad scope of the present invention.

The copper precursor formulations of the present invention are stable and have additional advantageous compositional and functional features, as hereinearlier described. In consequence of their stability, these formulations may be made up by a chemical supplier prior to shipment to the end user, and thereafter such formulations may be stably stored until they are required for use in the process. The formulation may then be supplied to a CVD tool by a single liquid supply line. Accordingly, an end user of the copper precursor formulation need not supply a separate water vapor (steam) line to the CVD process reactor. Further, the elimination of a separate water vapor (steam) flow reduces the number of process variables that need to be monitored, calibrated, adjusted, etc. In this manner, the hydrative copper precursor formulations of the invention may be readily and efficiently used to deposit copper in commercial semiconductor manufacturing operations.

Referring now to the drawings, FIG. 1 is a schematic representation of a liquid delivery MOCVD system 100 that may be employed in the practice of the invention for effecting copper metallization in the manufacture of semiconductor devices, or otherwise forming a copper-containing material on a substrate, using copper precursor formulations of the invention.

The delivery system 100 includes a first fluid feed passage 10 into which a first fluid is introduced in the direction indicated by arrow $F_1$. The first fluid may comprise a carrier gas, such as argon, as well as other gaseous components, e.g., volatile source compounds for other elements of the metal-containing film to be formed on the substrate.

The first fluid feed passage 10 is connected to a gas distribution manifold at its proximal end 11, and is open at its distal end 13. The distal portion 16 of passage 10 is mounted in a housing 12 of a reactor 14, such as a CVD growth chamber. The distal portion 16 of the first fluid feed passage 10 thus is centrally disposed in the cylindrical portion 15 of the CVD reactor 12, to form an annular interior volume 17 therebetween.

Communicating with the annular interior volume 17 is a second fluid flow passage 18, into which a second fluid is introduced for flow in the direction indicated by arrow $F_2$, through the open end 19 of the passage. The second fluid introduced in passage 18 to the reactor may include other source reagent materials, or components or carrier gas species, such as oxygen, argon, etc.

Disposed in the proximal portion 21 of the first fluid flow passage 10 is a flash vaporization element 26, which is joined in liquid delivery relationship to liquid reservoir 34 by conduit 28 and conduit 32, having check valve 30 therebetween. The liquid reservoir 34 may contain a copper precursor formulation according to the present invention. The copper precursor, if of solid form at ambient temperature conditions, may be dissolved or suspended in a compatible solvent medium, as more fully described in U.S. Pat. No. 5,820,664 issued Oct. 13, 1998 for "PRECURSOR COMPOSITIONS FOR CHEMICAL VAPOR DEPOSITION, AND LIGAND EXCHANGE RESISTANT METAL-ORGANIC PRECURSOR SOLUTIONS COMPRISING SAME," the disclosure of which is hereby incorporated herein by reference in its entirety.

Conduit 28 is sized and arranged (mounted on flash vaporization element 26) in such manner as to prevent premature evaporation of any volatile components (e.g., solvent constituents) of the precursor formulation flowed through the conduit to the flash vaporization element. Conduit 28 extends in the illustrative embodiment through the lateral extension 20 of the first fluid flow passage 10.

The delivery system 100 shown in FIG. 1 comprises a flash vaporization zone 22, which may be maintained at a suitable elevated temperature commensurate with the flash vaporization of the copper precursor formulation on the flash vaporization element 26.

Downstream from the vaporization zone 22 is an injection zone 24, wherein a second fluid may be introduced via the second fluid flow passage 18. The injection zone 24 is maintained at a suitable temperature, which may be somewhat less than the temperature of the vaporization zone, depending on the character of the various constituents introduced through the respective first and second fluid flow feed passages. In some instances of the present invention, it may be advantageous to introduce the copper precursor formulation into the system by injection via the injection zone.

In operation, the first fluid is flowed in the direction $F_1$ through the first fluid flow passage 10 into the reactor 12, being discharged at the distal open end 13 of the first fluid flow passage 10. Concurrently with such flow of gas therethrough, the precursor formulation from reservoir 34 is flowed through conduit 32, check valve 30, and conduit 28, to the flash vaporization element 26.

The flash vaporization element 26 may be formed of any suitable material that does not deleteriously interact with the reagent source liquid or other fluid species introduced into the first fluid flow passage. The flash vaporization element should also be heatable to sufficient elevated temperature to effect flash vaporization of the precursor formulation liquid that is introduced from conduit 28 onto the surfaces of the vaporization element. The vaporization element may for example be formed of metals such as stainless steel, copper, silver, iridium, platinum, etc., or alternatively from ceramics, high temperature glasses, composite materials, or the like, the choice of a specific material of construction being dependent on the temperature regime which is encountered by the vaporization element, as well as the composition of the copper precursor formulation and the composition of any other fluid flowed past the vaporization element in the first fluid flow passage 10.

Preferably, the vaporization element is constructed of an inert metal, and has a relatively high surface-to-volume ratio, as for example at least about 4, more preferably at least about 10, and most preferably at least about 100, when the surface and volume are measured in corresponding area and volume dimensional units (viz., square and cubic values of the same dimensional units, e.g., centimeters). The vaporization element is advantageously foraminous (i.e., porous or perforate) in character.

The flash vaporization element may take the form of a screen, porous sintered material body, grid, or the like. The composition, surface area, and surface-to-volume characteristics of the vaporization element are selected so as to effect flash vaporization of the copper precursor formulation on the surfaces of the structure, near contemporaneously with application of liquid thereto.

The conduit 28 introducing the copper precursor formulation onto the matrix structure 26 may simply be an open-ended tube, i.e., a tube whose open end communicates with the vaporization element, whereby liquid issuing from the conduit flows onto the surfaces of the element for flash vaporization thereon, when the element is heated to suitable elevated temperature. As previously discussed, conduit 28 is appropriately sized and arranged relative to the vaporization element 26 to prevent any undesirable premature evaporation of the copper precursor formulation before the flash vaporization thereof on the vaporization element.

In order to enhance the dispersion and distribution of the copper precursor formulation onto the surfaces of the vaporization element, the conduit 28 may have a restriction rod (not shown) centrally disposed therein to form an interior annular conduit, whereby pressure drop in the conduit is adjusted to a desired level, and whereby liquid appropriately issues in a thin film onto the vaporization element surfaces. Alternatively, the conduit 28 may be joined to a suitable nozzle or distributor means (not shown) at the distal end of the conduit, to facilitate distribution of the copper precursor formulation onto the vaporization element surfaces.

The precursor formulation reservoir 34 may be associated or otherwise coupled with a suitable liquid pumping means (not shown), such as a positive displacement liquid pump which effects discharge of the liquid copper precursor formulation from the reservoir through conduit 32, check valve 30, and conduit 28 to the vaporization element 26. The precursor formulation liquid may be introduced onto the vaporization element in a steady stream injection mode or in a pulsed injection mode from the conduit 28. In general, steady stream injection of the copper precursor formulation is desirable in CVD applications since it provides the most stable concentration of the copper precursor formulation in the downstream reactor, however, pulsed injection of the copper precursor formulation may be advantageous in some applications.

Preferably, the vaporization element 26 is formed of a material having a high specific heat capacity, so that the structure is substantially unaffected by heat of vaporization effects, whereby the vaporization element is suitably maintained at a desirable elevated temperature for continuous operation and vaporization of the copper precursor formulation. Materials of construction, such as iron, which may contaminate the deposited copper films sought to be formed from the precursor formulation liquid, should be avoided in the practice of the invention, in applications where the composition and stoichiometry of the deposited copper-containing film are critical.

The check valve 30 between conduits 28 and 32 controls the on/off flow of the precursor formulation liquid therethrough to the vaporization element 26 and is required to prevent the uncontrolled delivery of the precursor formulation to the vaporization element 26 under reduced pressure operating conditions.

The copper precursor formulation in liquid form is delivered to the heated vaporization element 26 where it is vaporized to form precursor vapor. The resultant precursor vapor is then carried by a first fluid (carrier gas) into the deposition reaction chamber 12 for deposit of copper-containing material on a substrate mounted in the deposition chamber. The first fluid may also comprise other reagents from various upstream bubblers or other source means therefor.

Figure 2:
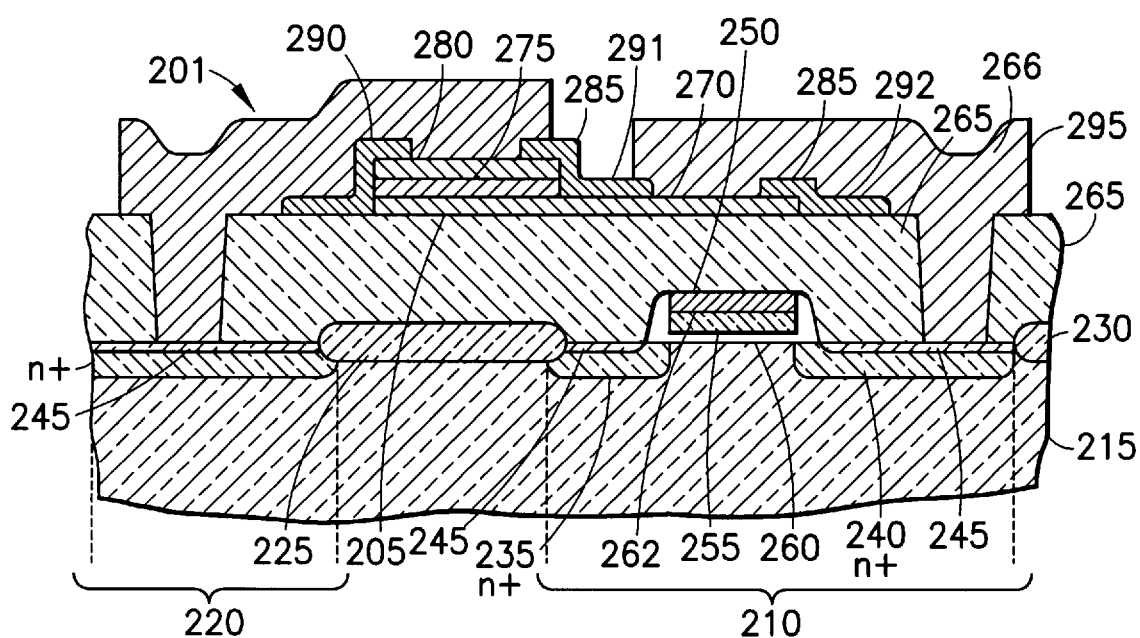
FIG. 2 schematically shows a portion of an exemplary integrated circuit (IC) with an integral capacitor that may be fabricated in accordance with the invention.

FIG. 2 schematically shows a portion of an exemplary integrated circuit (IC) device that may be fabricated in accordance with the invention. The illustrated portion of integrated circuit 201 includes a first active device 210, such as a conventional metal-oxide-semiconductor field effect transistor (MOSFET), and a capacitor 205 employing a dielectric film layer of (Ba,Sr) titanate formed on a substrate 215, such as a silicon substrate. A drain region of a second transistor 220 is also shown. The particular types of active devices employed, e.g., NMOS, PMOS or CMOS, are based on the desired operation of the integrated circuit. Other suitable active devices include, for example, bipolar junction transistors and GaAs MESFETs. The transistors 210 and 220 can be fabricated, for example, by conventional processing methods. In FIG. 4, the transistors 210 and 220 include field oxide regions, 225 and 230 which are formed, for example, by $SiO_2$ and operate as insulators between the transistor 210 and adjacent devices, such as the transistor 220. Source and drain regions 235 and 240 of the transistor 210 are formed by doping with n-type impurities, such as arsenic or phosphorus for NMOS. An optional layer of silicide 245 is deposited over the source and drain regions 235 and 240 to reduce the source and drain resistance, which enables greater current delivery by the transistor 210.

A gate 250 of the transistor 210 includes, for example, polysilicon 255 doped with an n-type impurity, such as by an implant or vapor doping. The gate polysilicon 255 is disposed on a $SiO_2$ spacer 260. An optional layer of silicide 262 is also deposited over the gate polysilicon 255 to reduce the electrical resistance of the gate 250. An insulating layer 265 of, for example, P-glass which is an oxide doped with phosphorus is then deposited on the transistors 210 and 220 to provide protection to the transistors 210 and 220 and to facilitate electrical connection. Contract windows 266 are then etched in the insulating layer 265 to expose the device gate 250 and source and drain regions, such as the regions 235 and 240. Although only the drain regions of the transistors 210 and 220 are exposed in the cross-section of the integrated circuit illustrated in FIG. 2, it should be readily understood that the gate and source are exposed at other areas of the integrated circuit 1 that are outside the illustrated cross-section.

The capacitor 205 includes a first electrode 270 formed on the insulating layer surface, a dielectric thin film region 275 on the first electrode 270, and a second electrode 280 formed on the dielectric film region 275 opposite the first electrode 270. It is possible for the first electrode 270 to have a two-layer structure. Such a structure is, for example, a layer of platinum formed over a layer of Ti-nitride. Platinum alone is not a suitable electrode material, however, since it adversely chemically reacts with silicon. As a consequence, a diffusion barrier is advantageously employed as the second electrode layer which is in contact with the insulating layer surface, to substantially prevent a chemical reaction between the platinum and the silicon of the substrate 215. Suitable thicknesses for each layer of the two-layer structure are in the range of 0.01 to 0.5 µm.

It is further possible for the first electrode 270 to be a single layer structure of an appropriate conductive material. Overall suitable thicknesses for the first electrode 270, whether a one or two layer structure, are in the range of approximately 0.1 to 0.5 µm. Thicknesses less than 0.1 µm are undesirable because of its high electrical resistance while thicknesses greater than 0.5 μm are generally disadvantageous because of high fabrication cost and poor adherence. The first electrode 270 is larger than the second electrode 280 to provide electrical connection to the first electrode 270.

After formation of the capacitor 205, an insulating material 285, such as, for example, $SiO_2$ is deposited on edge regions 290, 291 and 292 of the capacitor 205 to prevent short circuits between the first and second capacitor electrodes 270 and 280 when the interconnection layer is formed. A copper interconnection layer 295 is then formed on the insulation layer and corresponding etched contact windows, to electrically connect the devices 210 and 220 and the capacitor 205. The copper interconnection layer is formed by CVD using a copper precursor formulation in accordance with the present invention. In the integrated circuit 201, the drain 240 of the transistor 210 is electrically connected to the first electrode 270 of the capacitor 280 and the capacitor's second electrode 280 is electrically connected to the source of the transistor 220.

While the invention has been described herein with reference to specific features and illustrative embodiments, it will be recognized that the utility of the invention is not thus limited, but rather extends to and encompasses other features, modifications and alternative embodiments as will readily suggest themselves to those of ordinary skill in the art based on the disclosure and illustrative teachings herein. The claims that follow are therefore to be construed and interpreted as including all such features, modifications and alternative embodiments within their spirit and scope.

What is claimed is:

1. A copper precursor liquid composition, comprising:

a copper precursor; and at least one of water and a non-ligand organic hydrate.

2. The copper precursor composition of claim 1, comprising water.

3. The copper precursor composition of claim 1, comprising a non-ligand organic hydrate.

4. The copper precursor composition of claim 3, wherein the non-ligand organic hydrate is selected from the group consisting of cyclic and acyclic organic compounds having at least one functionality selected from the group consisting of ketone groups, hydroxy groups, amino groups, and combinations thereof.

5. The copper precursor composition of claim 3, wherein the non-ligand organic hydrate is non-fluorinated.

6. The copper precursor composition of claim 3, wherein the non-ligand organic hydrate comprises a hydrate of an organic compound selected from the group consisting of:

7. The copper precursor composition of claim 3, wherein the non-ligand organic hydrate comprises a hydrate of an organic compound formed by an amount of water that is greater than zero but less than ten molecules of water per molecule of organic compound.

8. The copper precursor composition of claim 3, wherein the non-ligand organic hydrate comprises a hydrate of an organic compound formed by an amount of water that is from about one to about six molecules of water per molecule of organic compound.

9. The copper precursor composition of claim 1, comprising water, and a solubilizing agent selected from the group consisting of alcohols, ethers, trioxane, and ketones.

10. The copper precursor composition of claim 9, wherein the solubilizing agent is an alcohol.

11. The copper precursor composition of claim 10, wherein said alcohol is selected from the group consisting of methanol, ethanol, isopropanol, tert-butanol and neopentanol.

12. The copper precursor composition of claim 9, wherein the solubilizing agent comprises an ether.

13. The copper precursor composition of claim 12, wherein said ether comprises one or more compounds selected from the group consisting of ethers of the formula $R^8$—O—$R^8$ and ethers of the formula $R^8$—O—$R^*$—O—$R^8$ where $R^8$ is $C_1$–$C_5$ alkyl and $R^*$ is $C_1$–$C_6$ alkylene.

14. The copper precursor composition of claim 9, wherein the solubilizing agent is trioxane.

15. The copper precursor of claim 9, wherein the solubilizing agent is a ketone.

16. The copper precursor of claim 9, wherein the solubilizing agent is a ketone of the formula $R^8$—CO—$R^8$ where $R^8$ is $C_1$–$C_5$ alkyl.

17. The copper precursor composition of claim 1, wherein the copper precursor is selected from the group consisting of (hfac)Cu(MHY), (hfac)Cu(3-hexyne), (hfac)Cu(DMCOD), (hfac)Cu(TMVS), Cu(II)(acac)$_2$, and Cu(II)(hfac)$_2$.

18. The copper precursor composition of claim 1, wherein the composition does not contain:

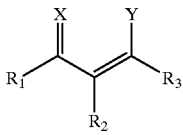

wherein $R_1$ and $R_3$ are independently selected from alkyl, aryl, fluoroalkyl or fluoroaryl; $R_2$ is halogen, alkyl, aryl, fluoroalkyl, or fluoroaryl; X and Y are selected such that when X=O, Y is OH, $NH_2$ or $N(R_4)H$, when X=NH, Y is $NH_2$ or $N(R_4)H$, when X=$NR_5$, Y is $(R_4)H$, and $R_4$ and $R_5$ are selected from the group consisting of alkyl, aryl, fluoroalkyl and fluoroaryl.

19. A copper precursor composition, comprising a copper precursor, water and a solubilizing agent for said copper precursor and water, whereby the composition is a homogeneous liquid composition.

20. A copper precursor liquid composition, comprising a copper precursor and a silanol water precursor.

21. The copper precursor composition of claim 20, wherein the water precursor decomposes to yield water and a volatile organic by-product under CVD process conditions.

22. The copper precursor composition of claim 20, wherein the water precursor comprises a component of the formula $R^7OH$, wherein $R^7$ is alkylsilyl.

23. The copper precursor composition of claim 22, wherein $R^7$ is $(Me)_3Si$.

24. The copper precursor composition of claim 22, wherein $R^7$ is $(Me)_x(R_A)_{(3-x)}Si$, x is from 0 to 3 and each $R_A$ is independently selected from the group consisting of $C_1$–$C_5$ alkyl.

25. A copper precursor composition including: a copper precursor comprising (hfac)Cu(MHY); and at least one of (a) water, (b) a water precursor and (c) a non-ligand organic hydrate.

26. A copper precursor liquid composition including: a copper precursor comprising (hfac)Cu(TMVS); and at least one of (a) water, (b) a water precursor and (c) a non-ligand organic hydrate.

27. A copper precursor composition including: a copper precursor comprising a copper complex of formula I:

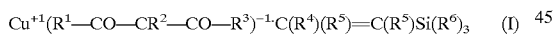

wherein $R^1$ and $R^3$ are each independently $C_1$–$C_8$ perfluoroalkyl, $R^2$ is H, F or $C_1$–$C_8$ perfluoroalkyl, $R^4$ is H, $C_1$–$C_8$ alkyl, or $Si(R^6)_3$, each $R^5$ is independently H or $C_1$–$C_8$ alkyl, and each $R^6$ is independently phenyl or $C_1$–$C_8$ alkyl and at least one of (a) water, (b) a water precursor and (c) a non-ligand organic hydrate.

28. A process for forming a copper-containing film on a substrate, comprising carrying out chemical vapor deposition with a copper precursor liquid composition comprising:
a copper precursor; and
at least one of water and a non-ligand organic hydrate.

29. The process of claim 28, wherein said chemical vapor deposition comprises liquid delivery chemical vapor deposition.

30. The process of claim 28, wherein said copper precursor composition comprises water.

31. The process of claim 28, wherein the copper precursor composition comprises a non-ligand organic hydrate.

32. The process of claim 31, wherein the non-ligand organic hydrate is selected from the group consisting of cyclic and acyclic organic compounds having at least one functionality selected from the group consisting of ketone groups, hydroxy groups, amino groups, and combinations thereof.

33. The process of claim 31, wherein the non-ligand organic hydrate is non-fluorinated.

34. The process of claim 31, wherein the non-ligand organic hydrate comprises a hydrate of an organic compound selected from the group consisting of:

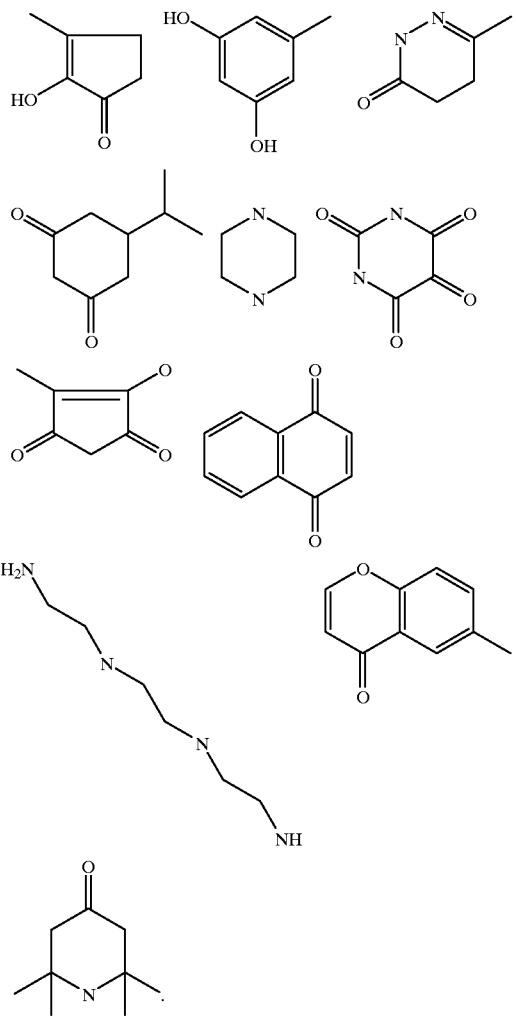

35. The process of claim 31, wherein the non-ligand organic hydrate comprises a hydrate of an organic compound formed by an amount of water that is greater than zero but less than ten molecules of water per molecule of organic compound.

36. The process of claim 31, wherein the non-ligand organic hydrate comprises a hydrate of an organic compound formed by an amount of water that is from about one to about six molecules of water per molecule of organic compound.

37. The process of claim 28, wherein the copper precursor composition comprises water, and a solubilizing agent selected from the group consisting of alcohols, ethers, trioxane, and ketones.

38. The process of claim 37, wherein the solubilizing agent is an alcohol.

39. The process of claim 38, wherein said alcohol is selected from the group consisting of methanol, ethanol, isopropanol, tert-butanol and neopentanol.

40. The process of claim 37, wherein the solubilizing agent comprises an ether.

41. The process of claim 40, wherein said ether comprises at least one compound selected from the group consisting of ethers of the formula $R^8$—O—$R^8$ and ethers of the formula $R^8$—O—$R^*$—O—$R^8$ where $R^8$ is $C_1$–$C_5$ alkyl and $R^*$ is $C_1$–$C_6$ alkylene.

42. The process of claim 37, wherein the solubilizing agent is trioxane.

43. The process of claim 37, wherein the solubilizing agent is a ketone.

44. The process of claim 37, wherein the solubilizing agent is a ketone of the formula $R^8$—CO—$R^8$ where $R^8$ is $C_1$–$C_5$ alkyl.

45. The process of claim 28, wherein the copper precursor is selected from the group consisting of (hfac)Cu(MHY), (hfac)Cu(3-hexyne), (hfac)Cu(DMCOD), (hfac)Cu(TMVS), Cu(II)(acac)$_2$, and Cu(II)(hfac)$_2$.

46. The process of claim 28, wherein the composition does not contain:

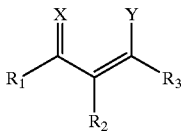

wherein $R_1$ and $R_3$ are independently selected from alkyl, aryl, fluoroalkyl or fluoroaryl; $R_2$ is halogen, alkyl, aryl, fluoroalkyl, or fluoroaryl; X and Y are selected such that when X=O, Y is OH, $NH_2$ or $N(R_4)H$, when X=NH, Y is $NH_2$ or $N(R_4)H$, when X=$NR_5$, Y is $(R_4)H$, and $R_4$ and $R_5$ are selected from the group consisting of alkyl, aryl, fluoroalkyl and fluoroaryl.

47. The process of claim 28, wherein the chemical vapor deposition comprises process conditions including a substrate temperature of from about 160° C. to about 230° C., a copper precursor composition vaporization temperature of from about 100° C. to about 300° C., a chemical vapor deposition pressure of from about 0.05 to about 20 Torr, and an inert carrier gas flow of from about 25 to about 750 sccm at the vaporization temperature.

48. A process for forming a copper-containing film on a substrate, comprising carrying out chemical vapor deposition with a copper precursor composition comprising a copper precursor, water and a solubilizing agent for said copper precursor and water, whereby the composition is a homogeneous liquid composition.

49. A process for forming a copper-containing film on a substrate, comprising carrying out chemical vapor deposition with a copper precursor composition comprising a copper precursor and a silanol water precursor.

50. The process of claim 49, wherein the water precursor decomposes to yield water and a volatile organic by-product in the chemical vapor deposition under CVD process conditions.

51. The process of claim 49, wherein the water precursor comprises a component of the formula $R^7OH$, wherein $R^7$ is alkylsilyl.

52. The process of claim 51, wherein $R^7$ is $(Me)_3Si$.

53. The process of claim 51, wherein $R^7$ is $(Me)_x(R_A)_{(3-x)}Si$, x is from 0 to 3 and each $R_A$ is independently selected from the group consisting of $C_1$–$C_5$ alkyl.

54. A process for forming a copper-containing film on a substrate, comprising carrying out chemical vapor deposition with a copper precursor liquid composition including a copper precursor comprising (hfac)Cu(MHY) and at least one of (a) water, (b) a water precursor and (c) a non-ligand organic hydrate.

55. A process for forming a copper-containing film on a substrate, comprising carrying out chemical vapor deposition with a copper precursor liquid composition including a copper precursor comprising (hfac)Cu(TMVS); and at least one of (a) water, (b) a water precursor and (c) a non-ligand organic hydrate.

56. A process for forming a copper-containing film on a substrate, comprising carrying out chemical vapor deposition with a copper precursor liquid composition including: a copper precursor comprising a copper complex of formula I:

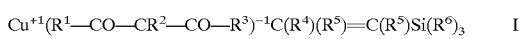

wherein $R^1$ and $R^3$ are each independently $C_1$–$C_8$ perfluoroalkyl, $R^2$ is H, F or $C_1$–$C_8$ perfluoroalkyl, $R^4$ is H, $C_1$–$C_8$ alkyl, or $Si(R^6)_3$, each $R^5$ is independently H or $C_1$–$C_8$ alkyl, and each $R^6$ is independently phenyl or $C_1$–$C_8$ alkyl; and at least one of (a) water, (b) a water precursor and (c) a non-ligand organic hydrate.

57. A method of metallizing a microelectronic device structure, comprising depositing on the microelectronic device structure a copper-containing film by chemical vapor deposition using a copper precursor liquid composition comprising:

a copper precursor; and at least one of water and a non-ligand organic hydrate.

58. Copper deposited on a substrate by the process of carrying out chemical vapor deposition with a copper precursor liquid composition comprising:

a copper precursor; and at least one of water and a non-ligand organic hydrate, to form a film of copper on the substrate.

59. An integrated circuit device including copper metallization formed by chemical vapor deposition with a copper precursor liquid composition comprising:

a copper precursor; and at least one of water and a non-ligand organic hydrate.

* * * * *

UNITED STATES PATENT AND TRADEMARK OFFICE
CERTIFICATE OF CORRECTION

PATENT NO : 6,102,993
DATED : August 15, 2000
INVENTOR(S) : Gautam Bhandari, et al.

It is certified that error appears in the above-identified patent and that said Letters Patent is hereby corrected as shown below:

Column 1, line 33,        delete "suicide" and substitute --silicide--

Column 10, line 34,       delete "5" before the word "temperature"

Signed and Sealed this

Seventeenth Day of April, 2001

*Attest:*

NICHOLAS P. GODICI

*Attesting Officer*        *Acting Director of the United States Patent and Trademark Office*